United States Patent [19]
Kurokawa et al.

[11] Patent Number: 5,923,020
[45] Date of Patent: *Jul. 13, 1999

[54] LIGHTING APPARATUS

[75] Inventors: Shuji Kurokawa, Ageo; Kenji Kobayashi, Omiya, both of Japan

[73] Assignee: LINTEC Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/621,694

[22] Filed: Mar. 26, 1996

[30] Foreign Application Priority Data

Mar. 31, 1995 [JP] Japan .................................. 7-100400

[51] Int. Cl.$^6$ .................................................. G06K 7/10
[52] U.S. Cl. ........................................ 235/454; 235/472
[58] Field of Search .................... 235/454, 472; 250/234

[56] References Cited

U.S. PATENT DOCUMENTS

| | | | |
|---|---|---|---|
| 3,617,759 | 11/1971 | Martin ..................................... | 250/234 |
| 3,757,125 | 9/1973 | Okada et al. ........................... | 250/234 |
| 3,860,935 | 1/1975 | Stauffer .................................. | 250/234 |
| 4,061,914 | 12/1977 | Green ..................................... | 250/234 |
| 4,603,976 | 8/1986 | Fetzer et al. ........................... | 235/455 |
| 4,805,175 | 2/1989 | Knowles ................................. | 235/472 |
| 4,893,223 | 1/1990 | Arnold . | |
| 5,091,636 | 2/1992 | Takada et al. .......................... | 235/472 |
| 5,185,638 | 2/1993 | Conzola et al. . | |
| 5,280,161 | 1/1994 | Niwa ...................................... | 235/462 |
| 5,350,909 | 9/1994 | Powell et al. .......................... | 235/472 |
| 5,463,213 | 10/1995 | Honda .................................... | 235/467 |
| 5,479,011 | 12/1995 | Rudeen et al. ......................... | 235/472 |
| 5,497,234 | 3/1996 | Haga . | |
| 5,661,290 | 8/1997 | Bard et al. .............................. | 235/462 |

FOREIGN PATENT DOCUMENTS

| | | |
|---|---|---|
| 0 183 946 A2 | 6/1986 | European Pat. Off. . |
| 6-317532 | 11/1994 | Japan . |

OTHER PUBLICATIONS

Patent Abstracts of Japan, from EPO, for Appln. No. 57–234 446, filed Dec. 24, 1982, publication No. 59–119 246, published Jul. 10, 1984.

Patent Abstracts of Japan, from EPO, for Appln. No. 60–136 160, filed Jun. 24, 1985, publication No. 62–011 133, published Jan. 20, 1987.

Patent Abstracts of Japan, from EPO, for Appln. No. 62–089 934, filed Apr. 14, 1987, publication No. 63–256 841, published Oct. 24, 1988.

*Primary Examiner*—Harold I. Pitts
*Attorney, Agent, or Firm*—Blank Rome Comisky & McCauley LLP

[57] ABSTRACT

A lighting apparatus 1 has a convex lens 11 arranged so that its optical axis is at an angle θ with respect to the normal of an observation portion 3a (e.g., a semiconductor substrate or the like), with a camera 5 arranged in the path of the reflected light rays. When a light-emitting portion 13 is arranged along the optical axis of the lens 11, a bright field illumination takes place. If a knob 29 is turned, the light-emitting portion 13 moves along a ball screw 25, thereby changing the illumination from a bright field illumination to a dark field illumination. When a knob 37 is turned, the light exiting the lens 11 will diverge if the light-emitting portion 13 is moved close to the lens 11, converge if the light-emitting portion 13 is moved far away from the lens 11, and be parallel if the light-emitting portion 13 is positioned at the focal point of the lens 11. By changing the position of the light-emitting portion 13 in this way, it is possible to change the illuminating angle and the illuminating angle distribution, and by adjusting the position of the light-emitting portion 13 in accordance with the optical characteristics of the object 3, it is possible to obtain a high contrast image. It is also possible for these adjustments to be carried out automatically by using an actuator, microcomputer or the like.

9 Claims, 13 Drawing Sheets

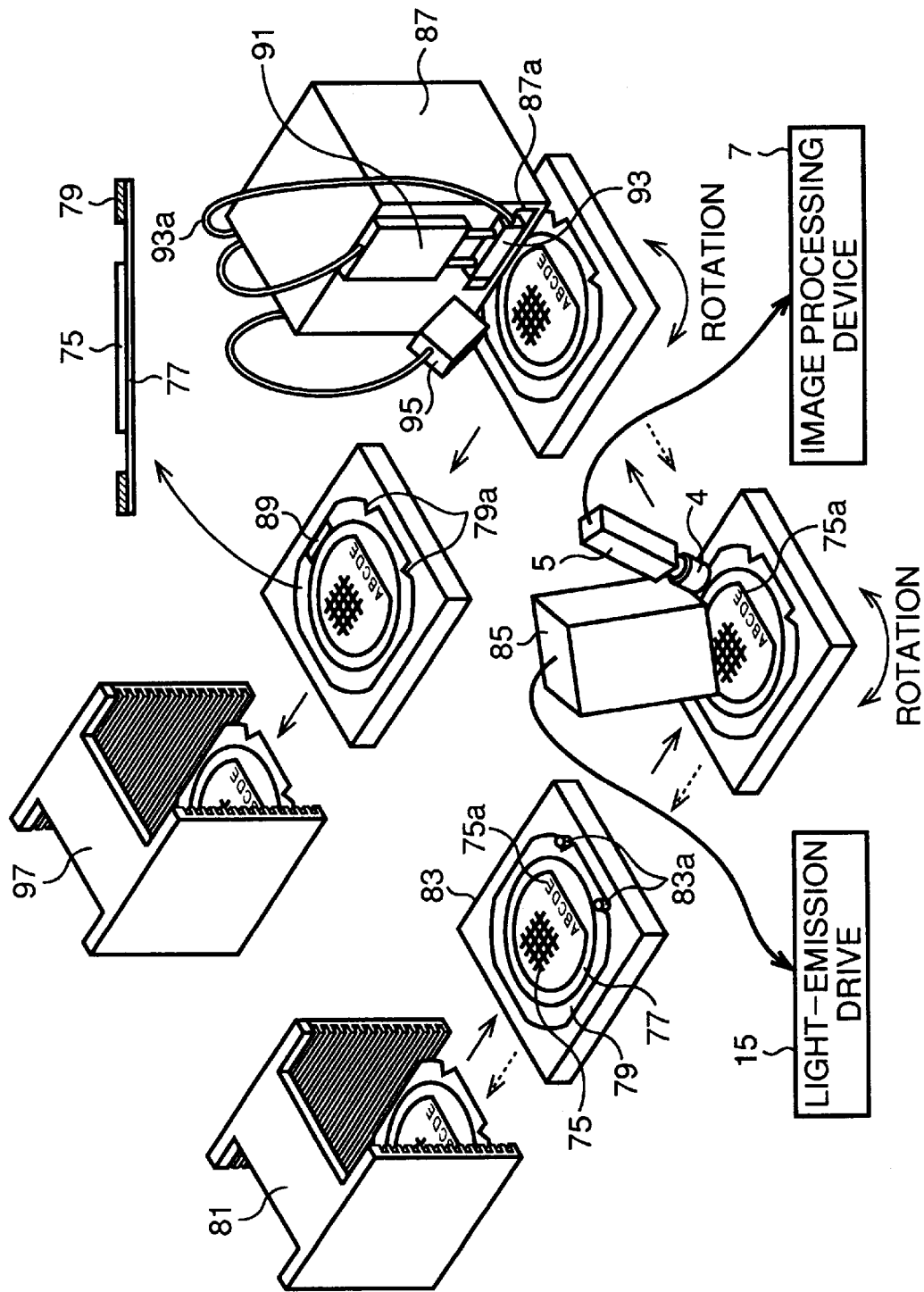

LIGHTING APPARATUS

BACKGROUND OF THE INVENTION

1. Field of the Invention

The present invention relates to a lighting apparatus, and in particular relates to a lighting apparatus for observing patterns such as circuitry, letters and the like which are formed on the surface or in the vicinity of the surface of an insulating substrate such as ceramic, glass, a semiconductor wafer or the like.

2. Description of the Prior Art

Up to now, during the manufacture of semiconductor integrated circuits and the like, microscopes, cameras and even the human eye have been used to observe patterns such as circuitry, letters and numbers which have been formed on the surface of a material such as resin, ceramic, glass, a liquid crystal substrate, a semiconductor wafer or the like. For example, during a manufacturing process, identification marks on a semiconductor wafer are read out, and then a predetermined process is carried out in accordance with such identification marks.

Several lighting apparatuses are known in the prior art for illuminating an object to be observed, and these apparatuses generally employ fluorescent lights, fiber optic illumination or a parallel light source comprised of lenses or the like.

When reading patterns such as letters or the like on a substrate, if there is a sufficiently large enough contrast between the pattern and the surrounding background, such pattern will be clearly seen, but if there is little contrast between the pattern and the surrounding background, it will be difficult to distinguish the pattern from the surrounding background. Such contrast between the pattern and the surrounding background is affected not only by the illuminance of the light source but also by the illuminating angle and the illuminating :angle distribution of the light source. "Illuminating angle distribution" means the distribution of illuminating angles within an observed area.

Although there is a bright field illumination for illuminating dark patterns on light backgrounds and a dark field illumination for illuminating light patterns on dark backgrounds, it is not necessarily a good idea to always employ a bright field illumination having a high illuminance.

Thus, in the lighting apparatuses of the prior art, it is necessary to consider the light source, the optical elements, the position of the object to be observed and the observer when determining the arrangement of the observation system in order to obtain a sufficiently large contrast at the portion being observed. Once this is done, it is then necessary to fix the positional relationship of such determined observation system; namely it becomes necessary to fix the illuminating angle and the illuminating angle distribution of the light which shines onto the object to be observed. In this regard, an operator must have sufficient experience and time to finely adjust the illuminating angle and the illuminating angle distribution.

In this connection, Japanese Laid-Open Patent Publication Nos. 6-3625 & 6-129844 disclose a semiconductor wafer inspection apparatus in which parallel light is shined onto a sample, with the reflected light or scattered light therefrom being focused by a convex lens toward an aperture stop arranged within the back focal plane of the convex lens. However, even in this type of apparatus, the illuminating angle and the illuminating angle distribution of the light is are fixed, and in order to finely adjust such illuminating angle and illuminating angle distribution, an operator must have sufficient experience and time.

Furthermore, even when observations are carried out using the same degree of illumination, there will be a wide variation in contrast due to the variation in optical characteristics of the object being observed as a result of differences in the manufacturing site, manufacturing apparatus or manufacturing process. In particular, there will be a wide variation in reflectance and transmittance due to warping of the object being observed and unevenness in the thickness of the pattern and surrounding material. Consequently, there will arise situations in which it is not possible to observe patterns due to low levels of contrast.

In such cases, for each observation, an optical axis adjustment which requires sufficient experience is carried out to obtain a high contrast for the object being observed. However, such adjustments require a great deal of time, and depending on the situation, there are many times in which an object must be treated as being unobservable.

To better understand this problem, a detailed description will be given for a sample semiconductor wafer. Namely, a semiconductor wafer has ID letters (identification marks) written into the top thereof by means of a write-in method, such as the same method used to form an integrated circuit pattern by means of photographic exposure or a method which employs a high-powered laser to etch letters into the top of the wafer. In general, ID letters are written on the wafer before the IC pattern is formed, after which each wafer undergoes a predetermined process in accordance with the ID letters thereof.

When such predetermined processes are carried out, a group of wafers called a "lot" undergo various treatments (vapor deposition, putting resist, exposure, etching, etc.). In this regard, it is quite common for each lot to undergo different treatments, and different processes need to be carried out depending on the type of IC being formed. Now, because such treatments are used to form several thin films on top of the wafer, various problems can arise as the processes involved in these treatments are carried out, such as warping of the wafer, the formation of uneven layers due to irregular resist in the vicinity of the ID letters, and damage to the wafer when conveyed from one location to another. These problems accumulate as the processes are carried out.

Now, in the prior art lighting apparatus, when a camera is used to observe the ID letters on top of a wafer which has undergone the various treatments described above, it is necessary to make the above-mentioned optical axis adjustments for each lot, each IC type and each ID writing method. In the case where it is not possible to carry out the adjustments, the light noise components due to irregular resist of the areas surrounding the ID letters combined with defects of the wafer will give rise to so-called image noise, and this can make it impossible to obtain the image of the ID letters. As a result, some cases need to be treated as unobservable.

SUMMARY OF THE INVENTION

In order to overcome the problems of the prior art described above, the present inventor carried out experiments to determine the relationship between the illuminating angle and the image formed. When the present inventor conducted such research, the positional relationship between a wafer, which comprised the object to be observed, and a camera and camera lens was fixed, with the illuminating angle and parallel characteristics of the illumination light being changed for various cases. The results of such research are as follows:

(1) There was more than one illuminating angle that can be used to make the wafer ID letters clearly visible from the surrounding portions of the wafer. Indeed, there was a plurality of continuous illuminating angle ranges which can be used. Further, there was a plurality of illuminating angle ranges which can be used to make any defects or unevenness of the wafer clearly visible. Moreover, there was also a plurality of illuminating angle ranges which have no effect on the ID letters or the defects and uneven portions of the wafer. It is possible to consider at least the wafers of the same lot as having roughly common properties, provided that the warping of each wafer is corrected.

(2) Depending on the method of writing in ID letters and the process for forming each type of IC, there were frequent cases in which the illuminating angle ranges (as mentioned in (1) above) and the number of such ranges were different for each lot.

(3) There were lots that did not necessarily require parallel illumination light. Indeed, there were cases where either converging light or diverging light was preferred.

From the results above, namely from the fact that there exists a plurality of preferred illuminating angle ranges and from the fact that the illumination light need not be parallel, the present inventor illuminated objects at various illuminating angles and at various illuminating angle distributions, and discovered an easy and fast way of carrying out illumination to obtain an image having a high degree of contrast. These discoveries enabled the present inventor to complete the present invention.

Namely, as shown in FIG. 1, in the lighting apparatus according to the present invention, light from a light-emitting portion 13 shines onto an object 3 via an optical element comprised of a convex lens 11. In this construction, the light-emitting portion 13 is made movable with respect to the convex lens 11 to permit adjustment of the illuminating angle.

The light which is reflected from the object 3 is directed toward an operator's eyes, a screen, a camera 5 or the like for observation. In particular, a bright field illumination is formed by placing the light-emitting portion 13 along the optical axis of the lens 11 for illuminating the object 3, and by arranging the camera 5 to lie within the path of the reflected light rays (as shown by the solid lines of FIG. 1). Now, if the light-emitting portion 13 is moved in the direction indicated by the arrow B, the light from the light-emitting portion 13 which is reflected by the object 3 will not enter the camera lens 4 of the camera 5, and this results in a dark field illumination (as shown by the broken line in FIG. 1). Furthermore, by slightly moving the light-emitting portion 13 in such direction, it becomes possible to make fine adjustments to the dark field illuminating angle.

Now, when the light-emitting portion 13 is moved in the direction indicated by the arrow A in FIG. 1, if such movement is towards the lens 11, the object 3 will be illuminated with divergent light rays, and if such movement is away from the lens 11, the object 3 will be illuminated with convergent light rays. In this connection, the direction of movement of the light-emitting portion 13 is not limited to the directions A, B shown in FIG. 1, and instead it is possible for the light-emitting portion 13 to be movable in any direction relative to the lens 11.

Further, in place of the-light-emitting portion 13, it is possible to use a plurality of light-emitting portions placed at different positions in a manner that allows such light-emitting portions to be selectively activated to emit illumination light.

Furthermore, as shown in FIG. 2, it is also possible to arrange the object 3 so as to be perpendicular to the optical axis of the convex lens 11. In this case, a half-mirror 41 is arranged between the light-emitting portion 13 and the convex lens 11 to direct the light reflected from the object 3 toward the camera lens 4. In the same manner as shown in FIG. 1, light from the light-emitting portion 13 shines onto the object 3 via the lens 11, and then the light reflected from the object 3 is directed toward the camera lens 4 by means of the lens 11 and the half-mirror 41. Now, if the light-emitting portion 13 is moved a distance "y" from the optical axis, the light reflected from the object 3 will not pass through the lens 11, and this results in a dark field illumination, as shown by the broken line in FIG. 2. In this connection, even in the case where this reflected light enters the lens 11, it is possible to prevent such light from entering the camera lens 4 by adjusting the distance "y" from the optical axis, and thereby to form a dark field illumination.

Now, when the light-emitting portion 13 is moved in the direction indicated by the arrow A in FIG. 2, namely along the direction of the optical axis, if such movement is towards the lens 11, the object 3 will be illuminated with divergent light rays, and if such movement is away from the lens 11, the object 3 will be illuminated with convergent light rays. Namely, the light rays which are close to the optical axis will be roughly parallel when they strike the object 3, and the light rays that are distant from the optical axis will shine on the object 3 at large angles. Furthermore, because the light-emitting portion 13 generally has a certain width which gives it more extent than a point light source, the light which shines onto the object 3 includes angular components which correspond to light emitted at certain distances from the optical axis. In other words, it becomes possible to obtain convergent light rays, divergent light rays and parallel light rays which make it possible to create an illuminating angle distribution.

Further, instead of moving a light-emitting portion, and instead of selectively activating a plurality of light-emitting portions, it is also possible to move a mask plate having at least one aperture arranged between the light-emitting portion 13 and the optical element 11.

Furthermore, instead of the above-mentioned mask plate, it is also possible to utilize an optical shutter element such as an LCD (liquid crystal device), PLZT (plomb lanthanum zirconate titanate), or the like. With such an optical shutter, it is possible to form any desired pattern via an appropriate electrical signal, and in this way it is possible to form any desired light-passage patterns or light-blocking patterns. For example, it is possible to select an appropriate signal which causes the optical shutter to have a light-passage pattern corresponding to the aperture of the mask plate and a light-blocking pattern which blocks off all other parts of the optical shutter.

Now, when the light-emitting portion 13 is moved with respect to the lens 11, or when a plurality of light-emitting elements is selectively activated to emit light, it becomes possible to selectively determine the illuminating angle and the illuminating angle distribution. In this way, it becomes possible to select an appropriate illumination (e.g., an illumination which will give a high contrast between what is to be read from an observation portion 3a and the surrounding background thereof) in order to obtain an optimum image.

In recent years, with the advances that have been made in thin film technology and photographic exposure technology for semiconductors, there is an increasing use of patterns formed on substrates which have optical characteristics that cause a high diffusion for illumination light in a prescribed direction. In particular, examples include patterns such as circuits and, letters and the like formed on semiconductor wafers, glass substrates for liquid crystals, ceramic materials, and resin substrates. In this regard, by illuminating such patterns with light in a prescribed direction, it is possible to obtain a high contrast when carrying out observations. Accordingly, by adjusting the illumination direction to match that of the prescribed direction, it is possible to obtain images having a high contrast.

Further, by moving the light-emitting portion 13 or by selecting the number of light-emitting elements, it is possible to finely adjust the illuminating angle and the illuminating angle distribution. For example, it is possible to easily switch between a bright field illumination and a dark field illumination, and it is also possible to easily generate parallel light, convergent light, divergent light and the like. Furthermore, it becomes possible to combine the light from a plurality of illuminating angles.

In this way, it becomes possible to carry out an optimum illumination in accordance with the optical characteristics of the object 3. Now, in the case where there are large irregularities in the optical characteristics of the object 3 due to irregularities and the like during the manufacturing process, it may not be possible to carry out a proper observation in accordance with one preferred illumination condition, but it is still possible to carry out an observation by switching between a plurality of illumination conditions. Accordingly, it is not necessary to perform the time-consuming optical adjustments required for prior art lighting apparatuses.

BRIEF DESCRIPTION OF THE DRAWINGS

FIG. 13 is an outline drawing of an eighth embodiment of the present invention.

DETAILED DESCRIPTION OF THE PREFERRED EMBODIMENTS

With reference to the drawings, descriptions of first to eighth embodiments according to the present invention will now be given.

First Embodiment

Figure 3:
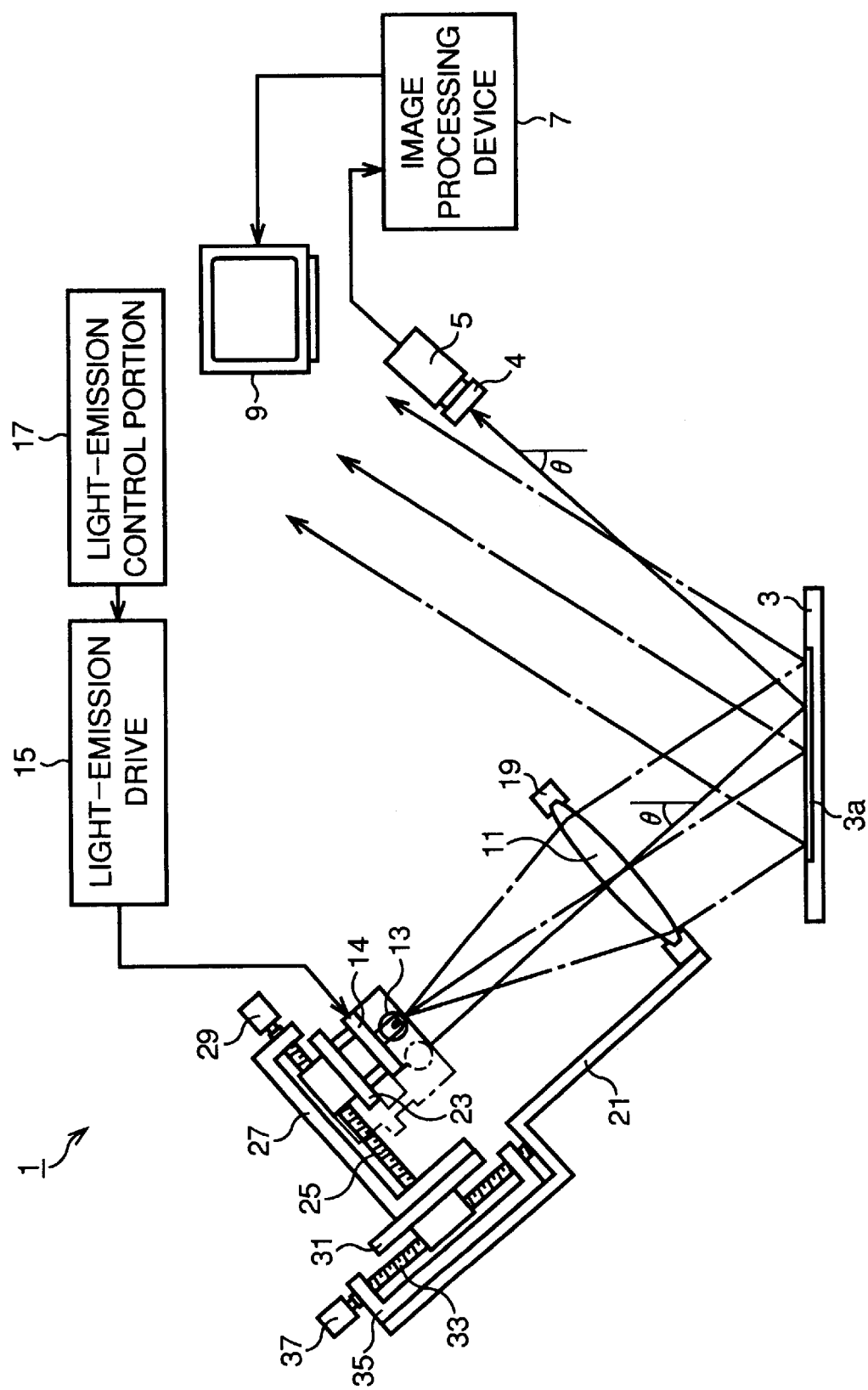
FIG. 3 is an outline drawing of a first embodiment of the present invention.

FIG. 3 shows a lighting apparatus 1 in accordance with the first embodiment of the present invention, in which the lighting apparatus is employed in a reading apparatus for reading out the identification marks on top of a substrate. As shown in FIG. 3, an object 3 (a semiconductor wafer or the like) has identification marks provided on an observation portion 3a thereof, and the light from the lighting apparatus 1 which shines onto this observation portion 3a is reflected therefrom and directed into a camera 5 via a camera lens 4. Image information from the camera 5 is inputted into an image processing device 7, which processes such information and outputs processed image signals (or unprocessed signals) to a display device 9, such as a CRT or the like, which displays images based on such processed image signals.

The lighting apparatus 1 is equipped with an optical element comprised of a thin convex lens 11, a light-emitting portion 13 which is freely movable in the vicinity of the focal point of the lens 11, light-emission drive 15 for driving the light-emitting portion 13, and a light-emission control portion 17 for controlling the light-emission drive 15. As for the positional arrangement of the light-emitting portion 13, it does not necessarily have to be in the vicinity of the focal point of the lens 11.

The lens 11 is held by a lens holder 19 which is fixed to a base 21 of the lighting apparatus 1. The light-emitting portion 13 is provided on a moving stage 23 via a holder 14, with the moving stage 23 being screwed onto a ball screw 25. The ball screw 25 is provided on a stage frame 27 so as to extend in a direction that is orthogonal to the optical axis of the lens 11. Provided at one end of the ball screw 25 is a graduated control knob 29 for controlling the position of the moving stage 23, whereby the moving stage 23 is moved along the ball screw 25 by turning the control knob 29. Namely, the position to which the stage 23 is moved is determined by the number of times the control knob 29 is turned in either the clockwise or counterclockwise direction. The stage frame 27 is fixed to a moving stage 31. The moving stage 31 is screwed onto a ball screw 33 which is provided on a stage frame 35 fixed to the base 21. The ball screw 33 extends in a direction that is parallel to the optical axis of the lens 11, and provided at one end of the ball screw 33 is a graduated control knob 37 for controlling the position of the moving stage 31, whereby the light-emitting portion 13 can be moved in the direction of the optical axis. Now, in the above construction, the moving stages 23, 31 can be moved by operating the control knobs 29, 37, respectively. However, in place of such control knobs 29, 37, it is also possible to utilize a motor, a motor drive and a motor controller to control the positions of the moving stages 23, 31.

As for the light-emitting portion 13, it is possible to utilize well-known lamps such as xenon lamps and halogen lamps. However, there is no restriction as to the type of light source which can be used for the light-emitting portion 13, and it is possible to use any appropriate light-emitting means, such as LEDs or the like. It is also possible to use end portions of light guiding elements such as optical fibers.

The light-emission drive 15 drives the light-emitting portion 13, and based on instructions from the light-emission control portion 17, the light-emitting portion 13 is switched ON or OFF and the intensity of the light emitted therefrom is regulated. The light-emission drive 15 may employ the holder 14, for example, as a circuit base which can hold both the light-emitting portion 13 and the circuit of the light-emission drive 15. Further, it is possible to improve the ability to reproduce illumination light at the same intensity by storing a detection value from a sensor or the amount of power needed for supplying the desired illumination intensity.

The light-emission control portion 17 is equipped with a control knob and a switch or the like for regulating the illumination intensity and for turning the light-emitting portion 13 ON or OFF, and based on the operations of such knob and switch, the light-emission control portion 17 controls the light-emission drive 15.

Further, it is also possible to arrange a moving mask plate (not shown in FIG. 3) between the lens 11 and the light-emitting portion 13. In this case, the moving mask plate is fixed to the moving stage 23 so as to move together with the light-emitting portion 13 and is provided with an aperture or pinhole to allow the light from the light-emitting portion 13 or only a portion of the light therefrom, to reach the lens 11. In this way, it is possible to create a sharper illuminating angle for the illumination light which shines on the observation portion 3a of the object 3.

Now, in the above construction, the lighting apparatus 1 is arranged such that the optical axis of the lens 11 forms an angle θ with respect to the normal of the observation portion 3a, with the camera being arranged in the path of the reflected light rays. As shown by the broken lines in the drawing, when the light-emitting portion 13 is positioned along the optical axis of the lens 11, a bright field illumination exists. If the knob 29 is turned, the light-emitting portion 13 moves along the ball screw 25, thereby changing the illumination from a bright field illumination to a dark field illumination. At this time, because the ray of bright field is generally strong with respect to the ray of dark field, by adjusting the switches and the like of the light-emission control portion 17, it is possible to lessen the difference between the ray of bright field and the ray of dark field, and this makes it possible to carry out even easier observations.

Also, by turning the knob 37, it is possible to change the position of the light-emitting portion 13 along the optical axis of the lens 11. In this regard, when the light-emitting portion 13 is positioned near the lens 11, the light exiting the lens 11 will diverge, and if the light-emitting portion 13 is positioned at the focal point of the lens 11, the light exiting the lens 11 will be parallel. Further, if the light-emitting portion 13 is moved away from the lens past such focal point, the light exiting the lens 11 will converge.

As described above, by changing the position of the light-emitting portion 13, it becomes possible to change the illuminating angle and the illuminating angle distribution, and this makes it possible to obtain images having an even higher contrast by carrying out adjustments while viewing the display device 9.

After adjustments, the image signal from the camera 5 is inputted into the image processing device 7, where the image is identified using well-known methods, and then the readout results are displayed by the display device 9. In this way, by changing the object 3, it is possible to read out the identification marks on observation portions 3a of any number of objects 3.

Although the ball screw 25 was described in the above embodiment as being arranged parallel to the focal plane of the lens 11, it is also possible for the ball screw 25 to be arranged at an angle with respect to such focal plane. In such case, when the moving stage 23 is moved, the light which shines on the observation portion 3a will be divergent, convergent or parallel depending on the position of the moving stage 23. Further, with either the ball screw 25 or ball screw 33 serving as an axle, it is possible to construct a rotatable light-emitting portion 13. Furthermore, the light-emitting portion 13 is not limited to movement along two axial directions, as was described in the embodiment above, and it is also possible for the lighting apparatus to be constructed so that the light-emitting portion 13 is able to move in three axial directions. In this way, it is possible to obtain an even wider range of illuminating angles and an even wider range of convergent or divergent illumination.

In the present embodiment, because the light-emitting portion 13 can be moved in directions that are parallel and perpendicular to the optical axis of the lens 11, there is little loss in the quantity of light which shines into the lens 11. For example, if the light-emitting portion 13 undergoes a pivotal type of movement instead of the parallel movement described for the present embodiment, the light sent toward the lens 11 will change directions, and this will result in a decrease in the amount of light entering the lens 11. In particular, because the space between the light-emitting portion 13 and the lens 11 is generally covered by a hood, as described hereinbelow, if the light-emitting portion 13 undergoes a pivotal movement, the ratio of light scattered by the hood will increase, resulting in a reduction of the light entering the lens 11. In contrast with this, in the present embodiment, there is very little loss in the amount of light entering the lens 11, and it is possible to change the illuminating angle. Namely, it is preferred that the light-emitting portion be capable of parallel movement, as shown in FIG. 3. In this respect, the embodiments shown in FIGS. 4, 5, 8, 9, 10 are able to achieve the same results.

Further, even though ball screws 25 and 33 were used in the present embodiment for respectively moving the moving stages 23, 31, the present invention is not limited to such construction, and it is also possible to use a piezo actuator, voice coil actuator, an air cylinder or the like, or a rotational actuator.

Furthermore, even though it is not shown in the drawings, it is also possible for the entire apparatus, excluding the illumination side of the lens 11, to be covered by a hood to prevent interference from outside light.

Second Embodiment

Figure 1:
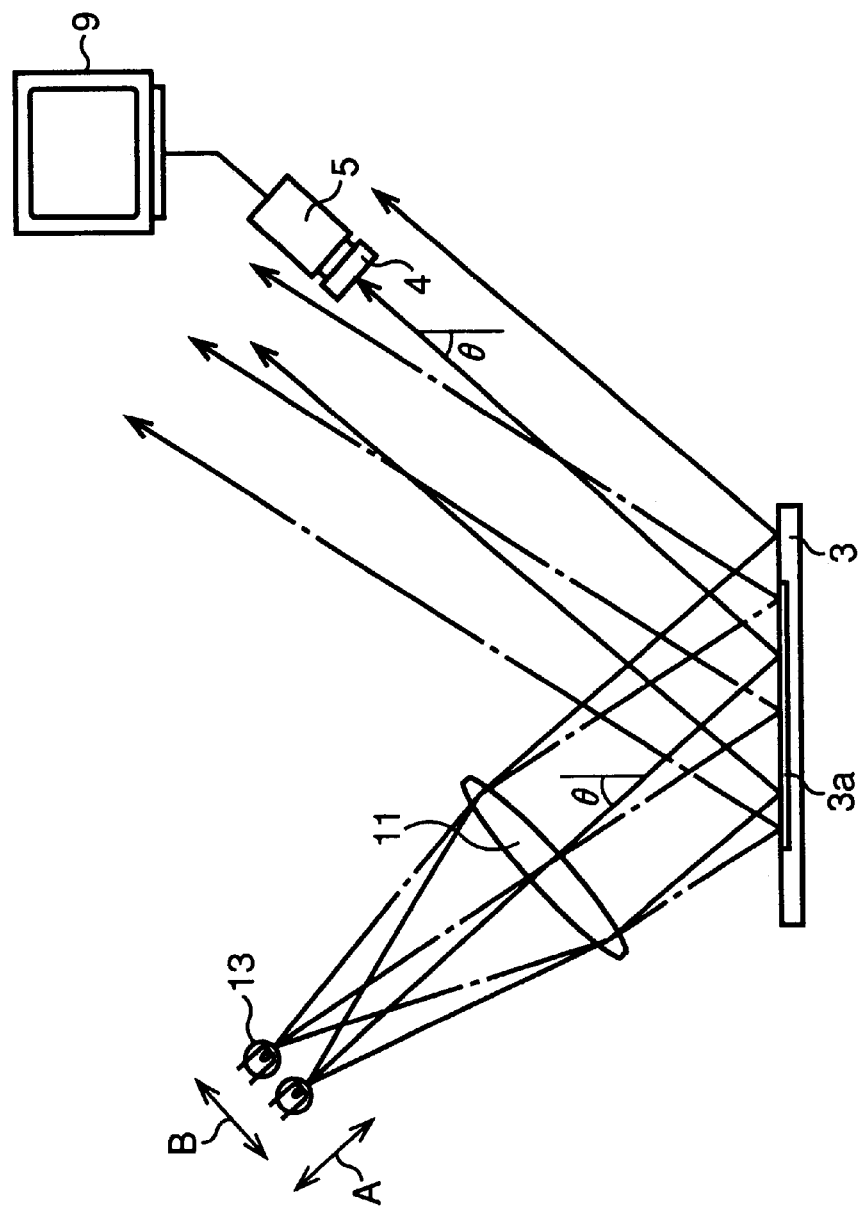
FIG. 1 is a drawing showing the principle of the resent invention.
Figure 2:
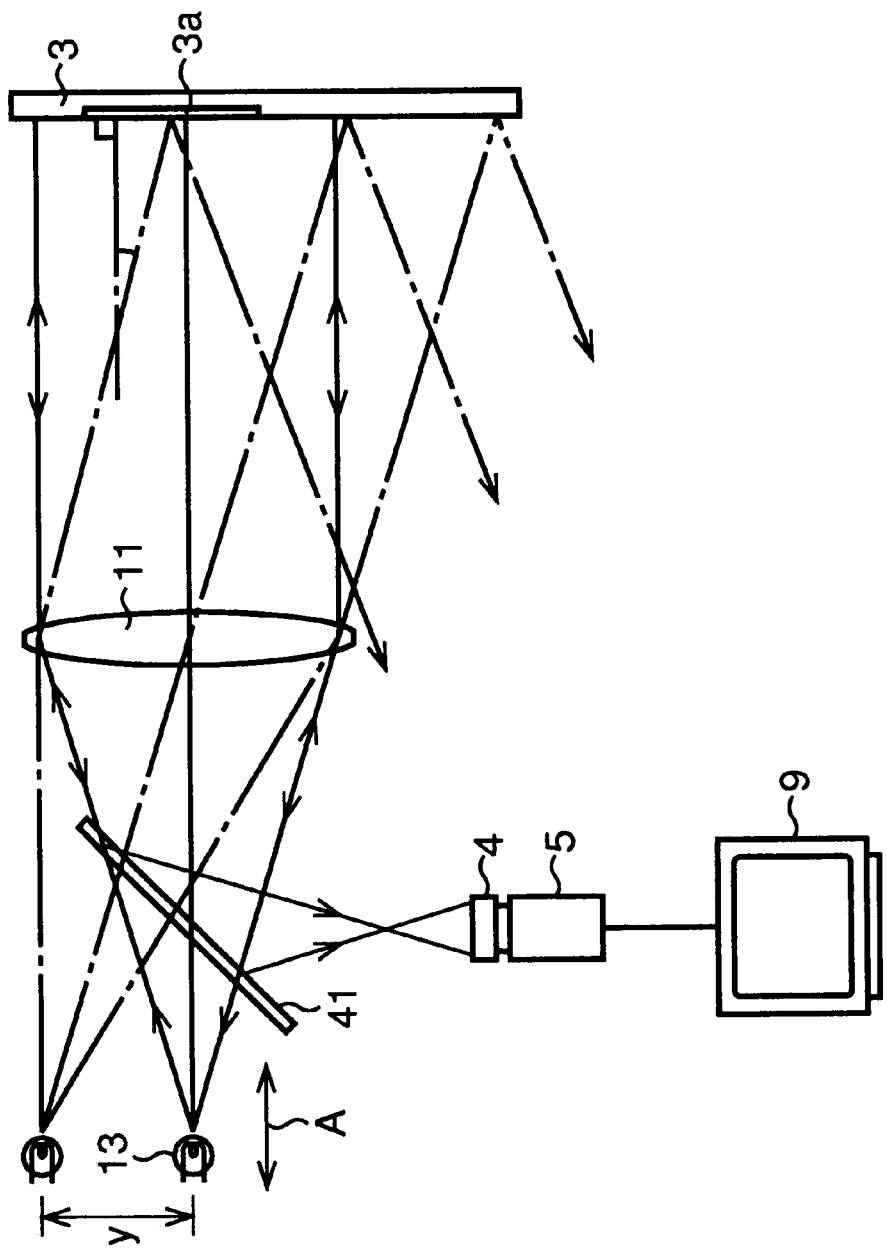
FIG. 2 is a drawing showing the principle of another arrangement of the present invention.
Figure 4:
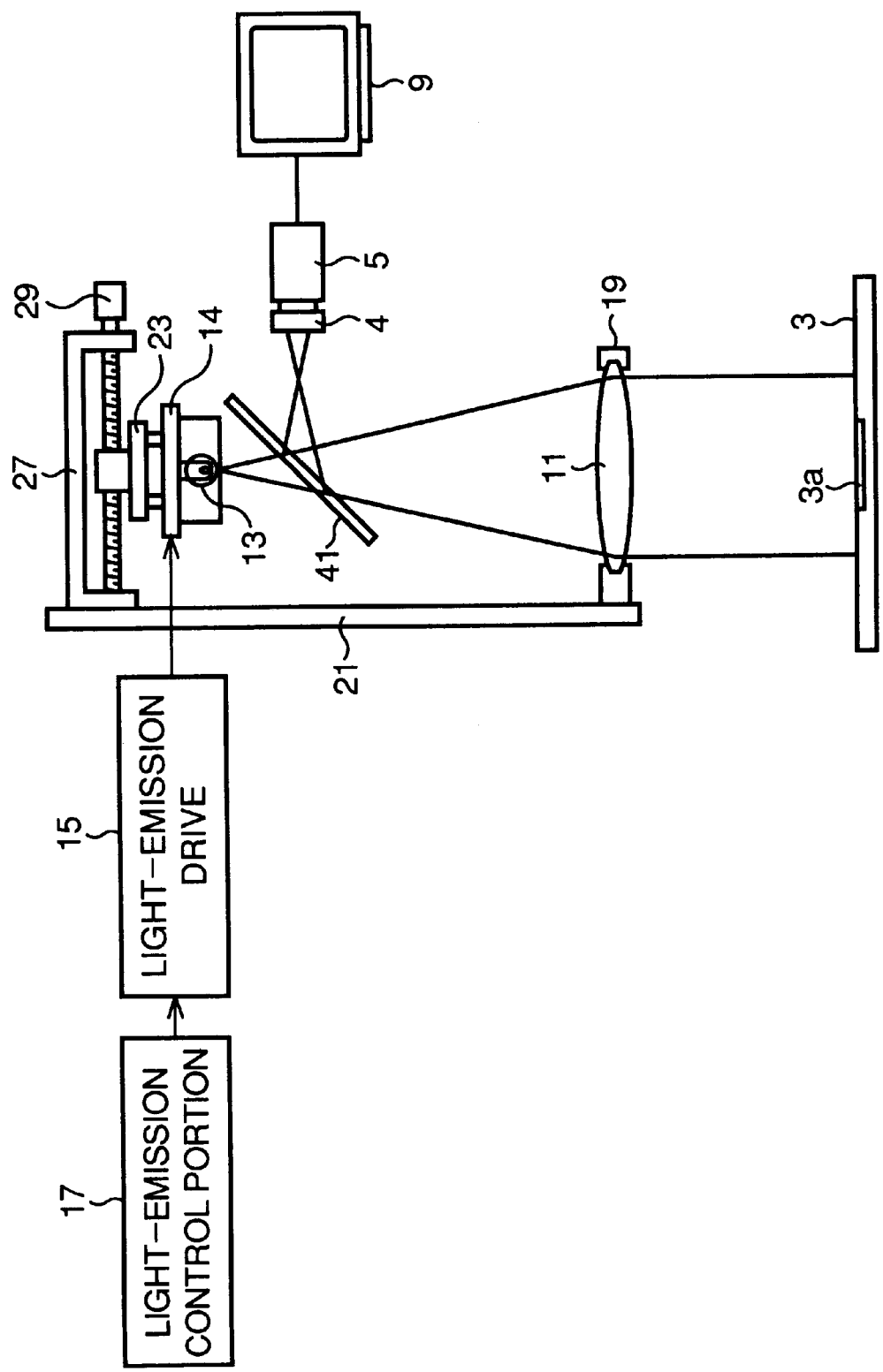
FIG. 4 is an outline drawing of a second embodiment of the present invention.

FIG. 4 shows a lighting apparatus according to a second embodiment of the present invention. In this embodiment, the object 3 is arranged perpendicular to the optical axis of the lens 11, and this corresponds to the principle-shown in FIG. 2. As shown in FIG. 4, those elements that perform the same function as the elements described above for the first embodiment are indicated by the same reference numerals.

However, this embodiment uses a half-mirror 41 which is arranged between the light-emitting portion 13 and the convex lens 11 at an angle of 45 degrees with respect to the optical axis of the lens 11.

In the construction shown in FIG. 4, the light which reflects off the object 3 is reflected by the half-mirror 41 into the camera lens 4, whereby an image is displayed on a display device 9. Now, if the knob 29 is turned, the holder 14 is moved in a horizontal direction, and this makes it possible to achieve a bright field illumination or a dark field illumination, and in accordance with the optical characteristics of the object 3, it is possible to obtain a high contrast image by adjusting the position of the light-emitting portion 13.

With the present embodiment, because the light reflected from the object 3 follows the light path in the opposite direction, it is possible to construct a compact lighting apparatus.

Third Embodiment

Figure 5:
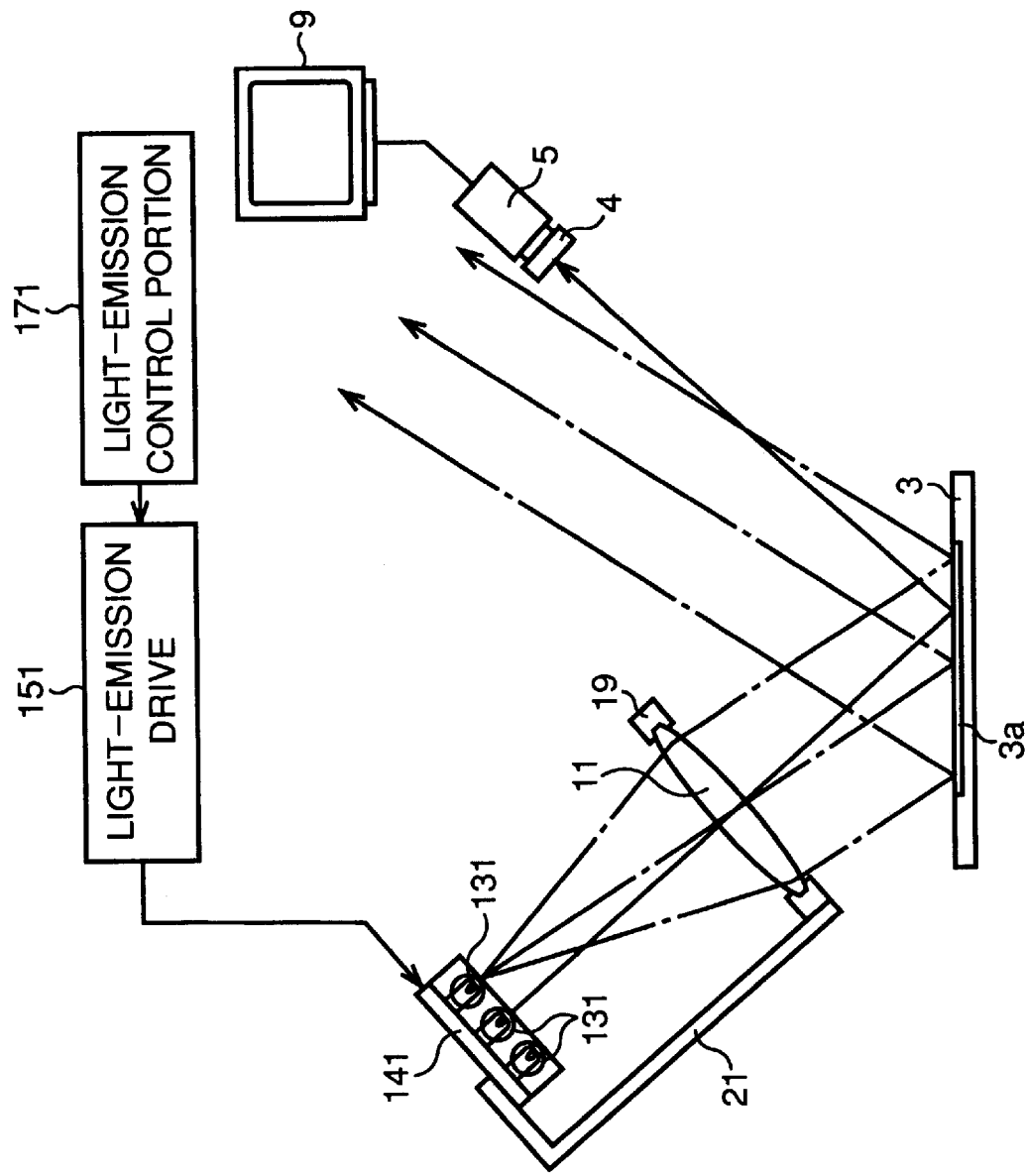
FIG. 5 is an outline drawing of a third embodiment of the present invention.

FIG. 5 is an outline drawing showing a third embodiment of a lighting apparatus according to the present invention. In this embodiment a holder 141 holds a plurality of light-emitting portions 131 (three portions are shown in the drawing), and light emission is carried out by switching between the light-emitting portions 131. The positional relationship between the light-emitting portions 131, lens 11, object 3 and camera lens 4 is the same as that shown in FIG. 3.

In this embodiment, a fight-emission drive 151 carries out switching operations between the light-emitting portions 131, and based on instructions from a light-emission control portion 171, each of the light-emitting portions 131 is switched ON or OFF and the intensity of the light emitted therefrom is regulated. In this connection, even though the drawing shows the light-emission drive 151 to be located apart from the holder 141, it is also possible for the holder 141 to act as a circuit substrate which holds the light-emitting portions 131 and the light-emission drive 151.

The light-emission control portion 171 is equipped with controls and switches for switching each of the light-emitting portions 131 ON or OFF and for regulating the intensity of light emitted therefrom, and by operating these controls and switches, it is possible to control the light-emission drive 151.

For the light-emitting portions 131, it is possible to use an arrangement of individual lamps or LEDs, or a collective arrangement of light-emitting elements, such as a lamp array, LED array or plasma display. In other words, it is possible to use any arrangement of light-emitting elements so long as it is possible to use the light-emission drive 151 and the light-emission control portion 171 to individually switch each element ON or OFF and to regulate the intensity of light therefrom;. Further, by arranging a mask plate or the like in front of the light-emitting portions 131, it is possible to carry out high contrast observations by restricting the light rays which enter the lens 11.

With this construction, by operating a switch provided for the light-emission control portion 171, it is possible to change the illuminating angle by selecting an appropriate light-emitting portion 131. For example, if the middle light-emitting portion 131 of FIG. 5 is selected, a bright field illumination will take place (as shown by the solid line in FIG. 5), and if the right end light-emitting portion 131 is selected, a dark field illumination will take place (as shown by the broken line in FIG. 5). In this way, a switching operation makes it easy to change the illuminating angle, whereby it becomes possible to quickly find the most appropriate illuminating angle for illuminating the observation portion 3a.

In this connection, the number of light-emitting portions 131 is not limited to three elements. Further, it is possible to use the light-emitting portions either one at a time or in combinations of two or more. In this regard, by increasing the number of light-emitting portions or the number of combinations of light-emitting portions which emit light at the same time, it becomes possible to illuminate the observation portion 3a at various illuminating angles, and because it takes very little time to carry out such switching operations, it becomes possible to quickly find the most appropriate illumination.

Further, the arrangement of light-emitting portions 131 is not limited to the arrangement shown in FIG. 5. For example, instead of the arrangement along a single axis shown in FIG. 5, it is possible to use a random arrangement of light-emitting portions, or it is possible to arrange the light-emitting portions along the optical axis or an axis that is at an angle with respect to the optical axis.

Figure 6:
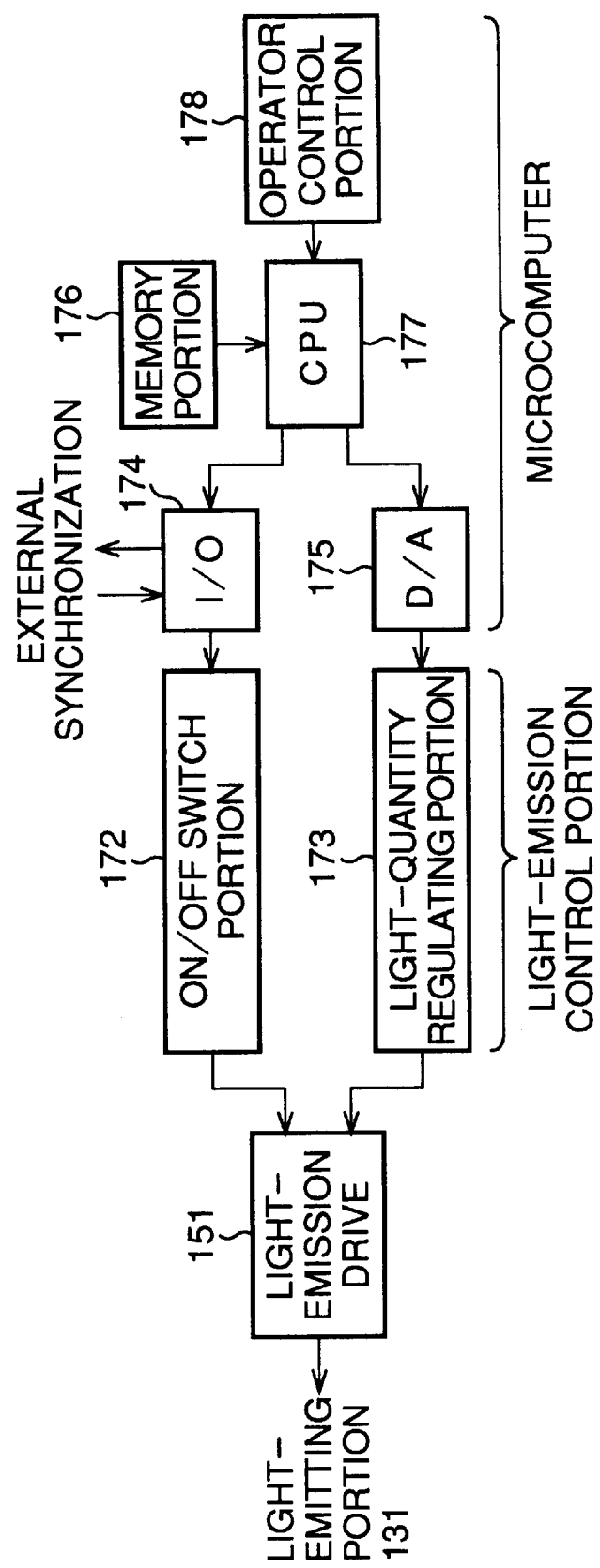
FIG. 6 is a block diagram of one example of a control device which uses a microcomputer to control the apparatus of FIG. 5.

Furthermore, while the operations of the light-emission control portion 171 may be carried out manually, it is also possible for such operations to be performed automatically by employing a microcomputer or the like. An example of such a case is shown by the block diagram of FIG. 6, in which the appropriate pattern of light-emitting portions and the intensity of the light emitted therefrom for observing a predetermined object 3 are stored in a vmemory portion 176 of a microcomputer 170 having a central processing unit (CPU) 177, with a microcomputer I/O portion 174 being connected to an ON/OFF switch portion 172 of a light-emission control portion via relays, transistors and the like (not shown). Further, a D/A converter 175 is connected to a light-quantity regulating portion 173 of the light-emission control portion 171, and in accordance with instructions from an operator control portion 178 of the microcomputer 170, it is possible to select one of several patterns appropriate for carrying out observations.

Furthermore, by providing an automatic conveying device for conveying the objects 3, by connecting the automatic conveying device and the camera 5 to an image processing device via the I/O portion 174, and by providing an external synchronization for the image processing device, it becomes possible to construct an automatic observation system. For example, upon receiving a signal indicating that the object 3 has reached a prescribed position, the microcomputer 170 can run one of many programs stored in the memory portion 176 to illuminate the object 3 at a prescribed illuminating angle and illuminating angle distribution. Then, upon receiving an instruction signal from the image processing device indicating that the identification marks of the object 3 have been read out, the microcomputer 170 can terminate the reading operation and instruct the automatic conveyer to convey the next object.

Fourth Embodiment

Figure 7:
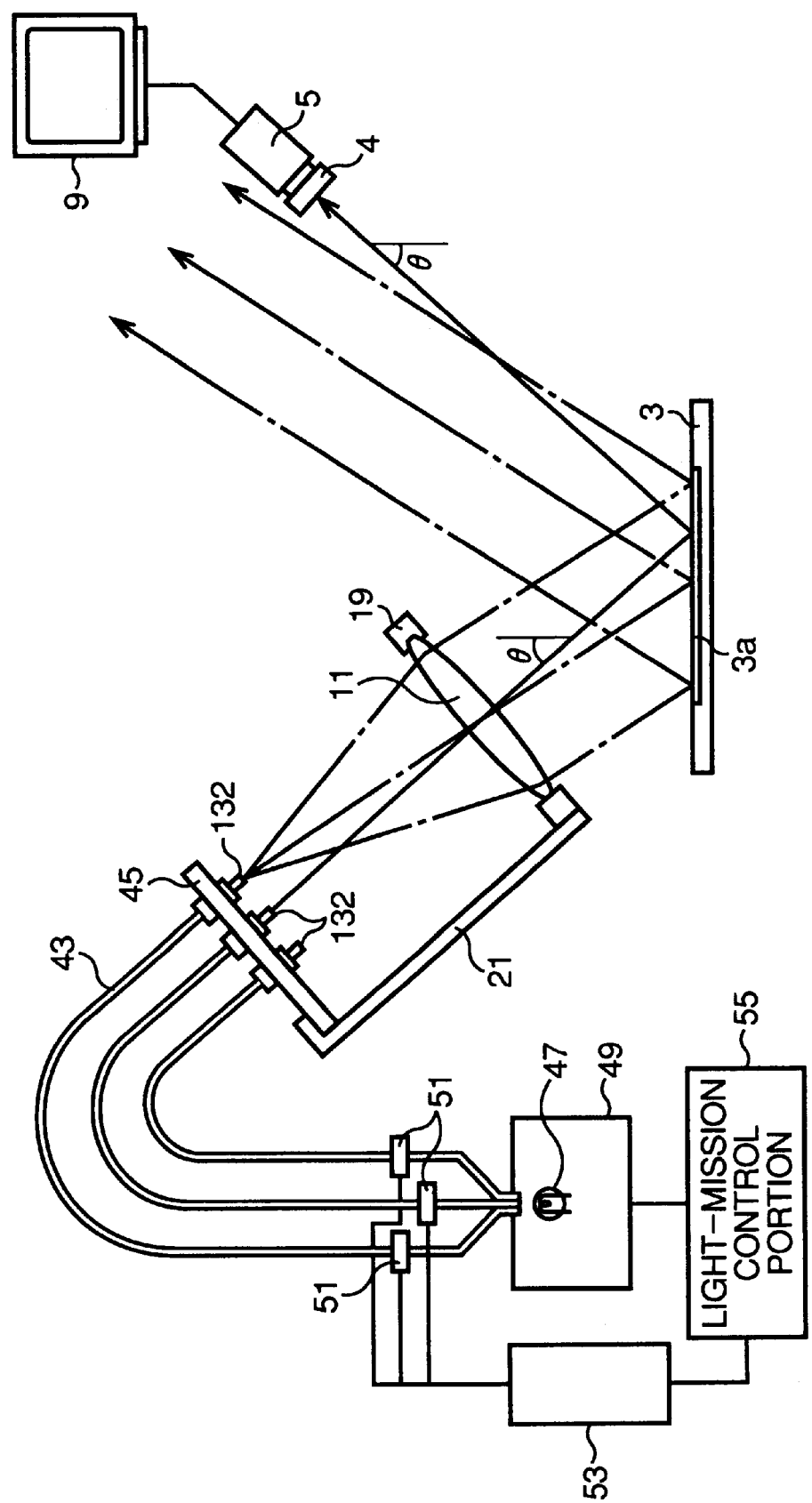
FIG. 7 is an outline drawing of a fourth embodiment of the present invention.

FIG. 7 shows a fourth embodiment of a lighting apparatus according to the present invention. In the present embodiment, light-emitting portions 132 employ end portions of at least one optical fiber bundle 43 (light-guiding element). In the example shown in FIG. 7, three light-emitting portions 132 are used. The light-emitting portions 132 are fixed to a light-emission portion holder 45, and the other ends of the optical fiber bundles 43 are connected to a light-emitting element 47 which is operated by a light-emission drive 49. Provided at a specific location along the length of each optical fiber bundle 43 is a shutter portion 51 which has a shutter that is controlled by a shutter drive 53 to open or close the fiber light path. The light-emission control portion 55 is connected to the light-emission drive 49 and the shutter drive 53 in order to control the ON/OFF operations of the light-emitting portion 132 and the open/close operations of the shutters in shutter portions 51.

In the lighting apparatus of the present embodiment, with the lens 11 arranged so that its optical axis is placed at an angle $\theta$ with respect to the normal of the observation portion 3a, and by arranging an observer's eye or a camera 5 at a position along the optical axis of the lighting apparatus at the side for receiving light reflected from the observation portion 3a, the observation portion 3a can be illuminated at a prescribed illuminating angle in accordance with the position of each light-emitting portion 132, and this makes it possible to carry out observations with the naked eye or a display device 9. Further, by operating the light-emission control portion 55, each of the light-emitting portions 132 can be switched ON or OFF, and this makes it possible to carry out illumination with the light-emitting portions 132 either separately or in one of several combinations with each other. In this way, it possible to observe the observation portion 3a at different illuminating angles.

In the present embodiment, because the light-emitting portions 132 are arranged along a line which is perpendicular to the optical axis of the lens 11, there is very little reduction in the amount of light which enters the lens 11 when switching from one light-emitting portion 132 to another. As was explained above for the first embodiment, if the end of an optical fiber bundle 43 undergoes a pivotal movement, such pivotal movement can cause the light which is directed toward the lens 11 to change direction, and this can result in a reduction in the amount of light which enters the lens 11. Further, if the space between the light-emitting portions 132 and the lens 11 is covered by a hood, the ratio of light scattered by the hood will increase, and this can also result in a reduction in the amount of light which enters the lens 11. Accordingly, as in the embodiment shown in FIG. 7, it is preferred that the light-emitting portions 132 be arranged parallel to the lens 11 because the reduction in the amount of light entering the lens 11 is small for parallel movement of a light source. Furthermore, if the end of an optical fiber bundle 43 undergoes pivotal movement, it is possible for the bundle 43 to break at a specific portion which bears a load. In response to this problem, in the present embodiment, the ends of the optical fiber bundles 43 are fixed in place so that they do not undergo any movement, and this eliminates the risk that a bundle might break.

Furthermore, it is possible to eliminate the shutter portions 51 from the embodiment shown in FIG. 7, and in their place arrange a light-emitting element at the light-receiving end of each optical fiber bundle 43, and then by switching such light-emitting elements ON or OFF, it is possible to switch each of the light-emitting portions 132 ON or OFF.

Fifth Embodiment

Figure 8:
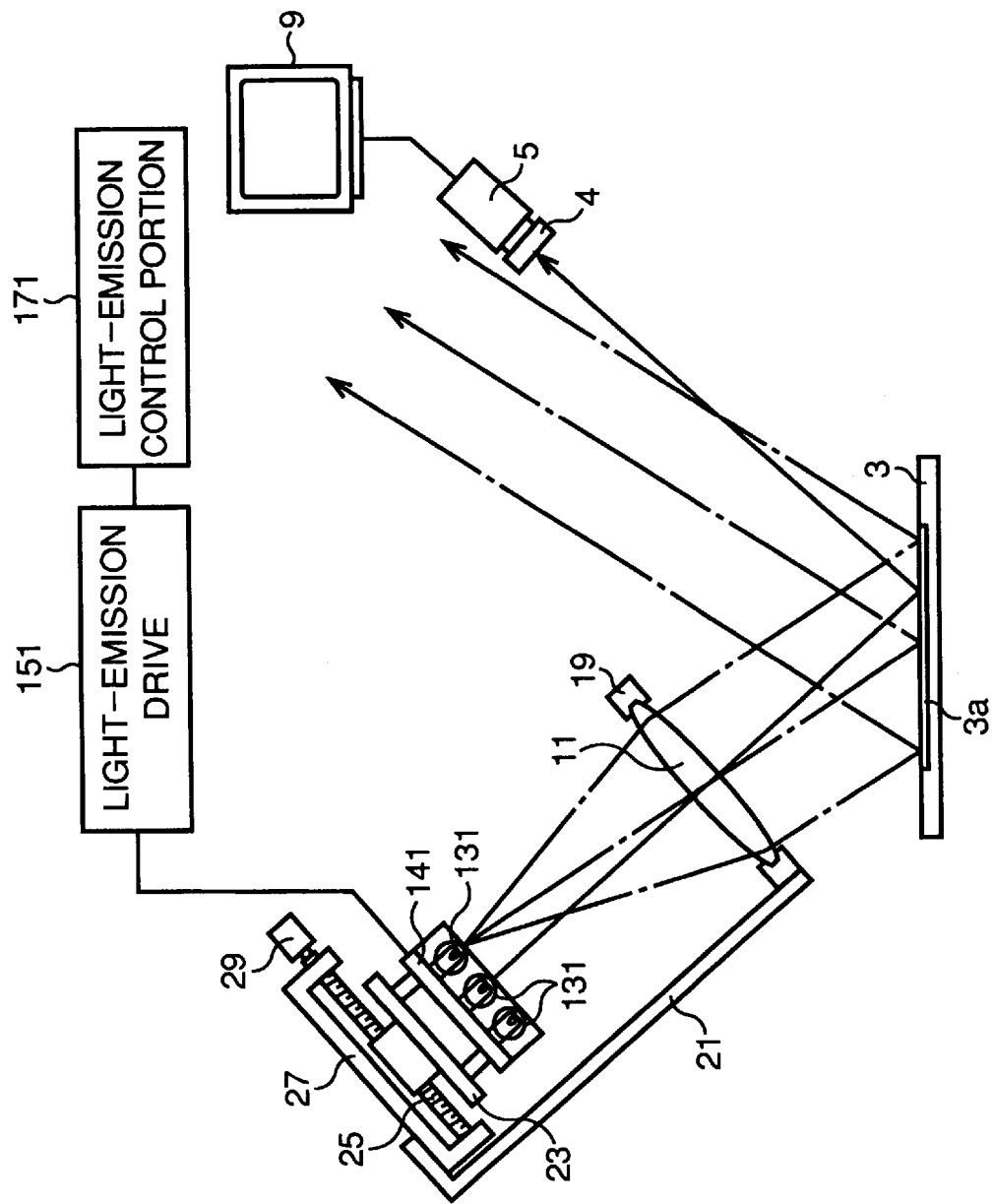
FIG. 8 is an outline drawing of a fifth embodiment of the present invention.

FIG. 8 shows a fifth embodiment of a lighting apparatus in accordance with the present invention. This embodiment is essentially a combination of the first embodiment (FIG. 3) and the third embodiment (FIG. 5). Namely, the arrangement of three light-emitting portions 131 shown in FIG. 5 is provided on the moving stage 23 shown in FIG. 3. Now, since the other elements of the present embodiment are the same as those shown in FIGS. 3 and 5, they are indicated by the same reference numerals.

With the embodiment of FIG. 8, it is possible to change the illuminating angle by selecting one or a combination of the light-emitting portions 131, and because the position of the light-emitting portions 131 can be changed by moving the moving stage 23, it is possible to carry out even finer adjustments on the illuminating angle.

Sixth Embodiment

Figure 9:
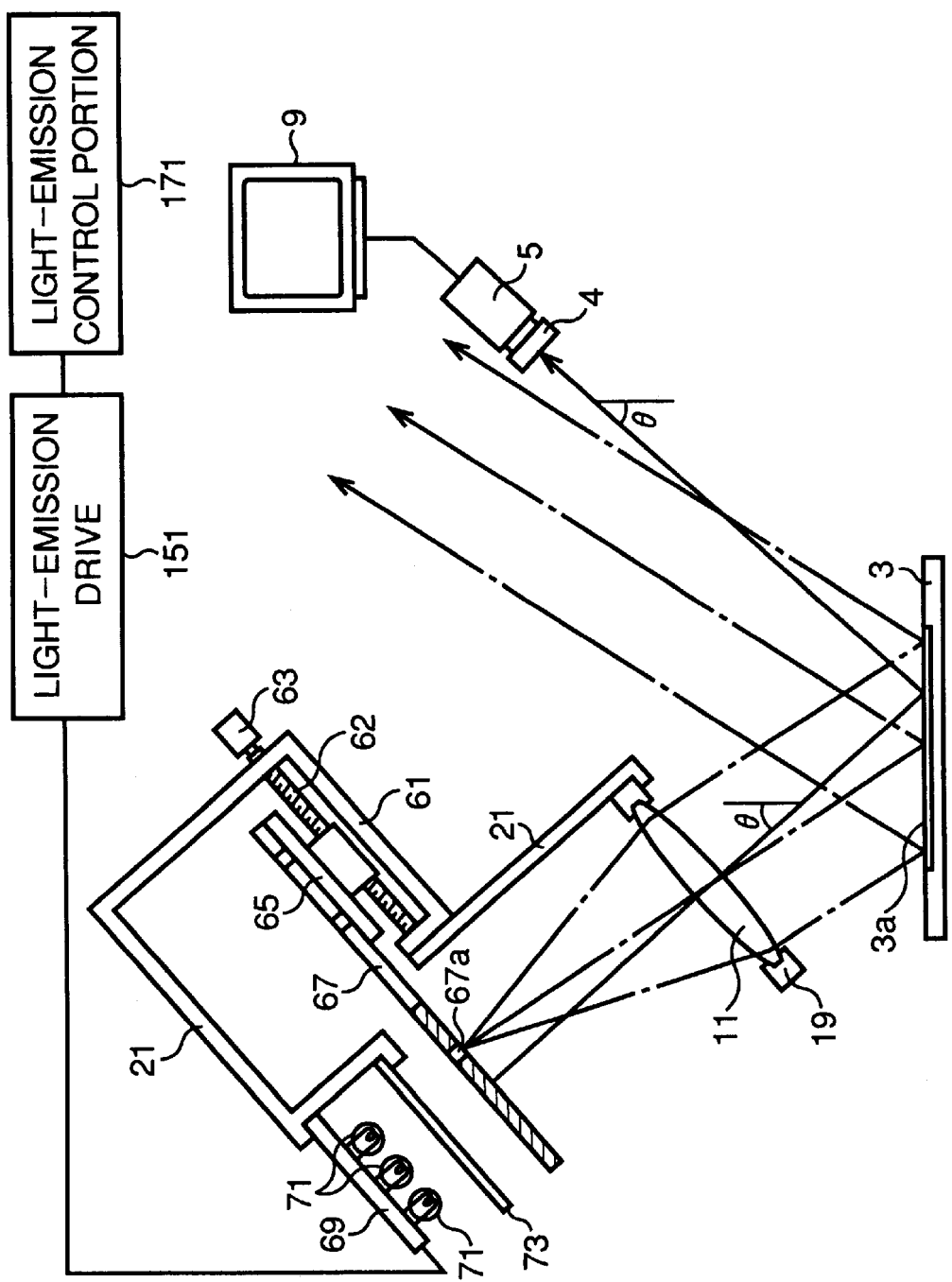
FIG. 9 is an outline drawing of a sixth embodiment of the present invention.

FIG. 9 shows a sixth embodiment of a lighting apparatus according to the present invention. In this embodiment of a lighting apparatus, a convex lens 11 is supported by a lens holder 19 which is fixed to a base 21. The base 21 is connected to a stage frame 61 which is provided with a ball screw 62, and provided on the ball screw 62 is a moving stage 65 which is freely movable. The moving stage 65 is moved with respect to the stage frame 61 by operating a stage position adjustment knob 63. Fixed to the moving stage 65 is a mask plate 67 which has an aperture portion 67a formed in at least one location for allowing light to pass therethrough. Further, the mask plate 67 is arranged in the vicinity of the front focal point of the lens 11. Provided at an upper portion of the base 21 is a light-emitting portion holder 69 which holds a plurality of light-emitting portions 71. Provided on the base 21 at a position in front of the light-emitting portions 71 is a diffusion plate 73 for diffusing the light emitted from the light-emitting portions 71. The light-emitting portions 71 and the diffusion plate 73 may comprise any construction that allows a surface illumination to be carried out. In this connection, even though the diffusion plate 73 is not an essential element, by arranging the diffusion plate 73 between the light-emitting portions 71 and the mask plate 67 to carry out surface illumination, it is possible to avoid having to make adjustments for the relationship between the light-emitting portions 71 and the aperture portion 67a.

The light-emitting portions 71 are operated by a light-emission drive 151, and a light-emission control portion 171 is connected to the drive 151 to control the ON/OFF switching operations of the light-emitting portions 71 and to adjust the intensity of light emitted therefrom.

In the lighting apparatus of the present embodiment, the lens 11 is arranged so that its optical axis is placed at an angle $\theta$ with respect to the normal of the observation portion 3a, and an observer's eye or a camera 5 is arranged at a position along the optical axis of the lighting apparatus at the side for receiving light reflected from the observation portion 3a. The light from the light-emitting portions 71 enters the lens 11 after passing through the diffusion plate 73 and the aperture portion 67a. If the knob 63 is operated to move the moving stage 65, the aperture portion 67a will be moved within the focal plane of the lens 11. Namely, if the aperture portion 67a is aligned with the optical axis of the lens 11, the light which exits the lens 11 will be parallel, and this will result in a bright field illumination (as shown by the solid line in FIG. 9), and if the aperture portion 67a is positioned away from the optical axis, the observation portion 3a will be illuminated at a different illuminating angle in accordance with the distance of the aperture portion 67a from the optical axis, and this will result in a dark field illumination (as shown by thee broken line in FIG. 9).

In this connection, by forming two or more aperture portions 67a in the mask plate 67, it is possible to illuminate the observation portion 3a at a combination of illuminating angles and thereby achieve an even more appropriate illumination. Further, it is also possible to make the mask plate 67 movable along the optical axis of the lens 11. Furthermore, it is possible to switch between a plurality of mask plates having apertures of various size or formed at different locations.

Seventh Embodiment

Figure 10:
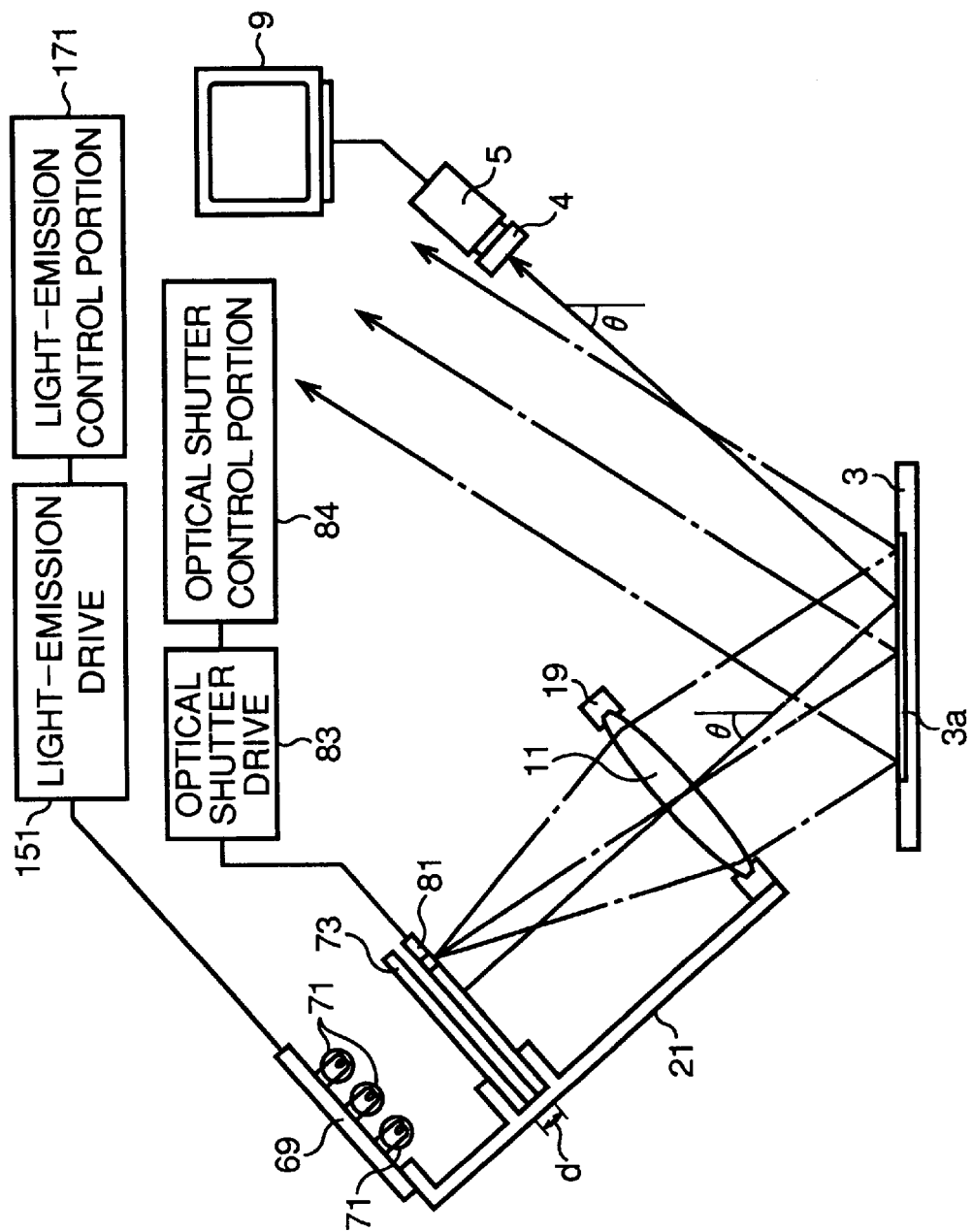
FIG. 10 is an outline drawing of a seventh embodiment of the present invention.

FIG. 10 shows a seventh embodiment of a lighting apparatus according to the present invention. In this embodiment, the mask plate of FIG. 9 is replaced by an optical shutter. As for the other elements of the present embodiment, the elements that are the same as those shown in FIG. 9 will be indicated by the same reference numerals.

Provided between the lens 11 and the diffusion plate 73 is an optical shutter 81 which is fixed to the base 21. The optical shutter 81 is an optical element, such as LCDs, PLZTs or the like, comprising transference electrodes with a specific material provided between such electrodes, and when electrical energy such as a voltage potential is supplied or interrupted to at least one specified space between the electrodes, the material lying therebetween becomes transparent or opaque. In this connection, a optical shutter drive 83 is provided to supply or interrupt electrical energy to specific electrodes of the optical shutter 81 in order to create transparent or opaque portions. Further, an optical shutter control portion 84 is provided to instruct the optical shutter drive 83 to create specific transparent and opaque portions in the optical shutter 81.

In this embodiment, it is also possible to employ a plurality of stacked shutters 81 to create an even better ability to block out light. In this way, by preventing light from leaking from the light blocking portions of the shutters 81, it becomes possible to obtain an even higher contrast when illuminating the observation portion 3a.

Now, in the case where an LCD is used for the shutter 81, it is necessary to use a polar screen with the LCD. Then, by providing one more polar screen at the observation side (e.g., directly in front of the camera lens 4 or an observer's eye), it becomes easy to carry out polarized observation.

In the embodiment shown in FIG. 10, each structural element is fixed to the base 21 in order to fix the position thereof, and except for the portion of the lighting apparatus where illumination light exits the lens 11, it is possible to cover the entire lighting apparatus with a hood to eliminate the effects of outside light.

In the lighting apparatus of the present embodiment, with the lens 11 arranged so that its optical axis is placed at an angle $\theta$ with respect to the normal of the observation portion 3a, and by arranging an observer's eye or a camera 5 at a position along the optical axis of the lighting apparatus at the side for receiving light reflected from the observation portion 3a, the observation portion 3a can be illuminated at a prescribed illuminating angle in accordance with a created transparent portion of the optical shutter 81, and this makes it possible to carry out observations.

Further, by operating the optical shutter control portion 84 to create two or more transparent portions in the optical shutter 81, it is possible to illuminate the observation portion 3a at a combination of illuminating angles, and thereby achieve an even more appropriate illumination. Furthermore, it is possible to create a plurality of transparent portions having different shapes at various prescribed locations of the optical shutter 81.

In this connection, FIGS. 11(a)–11(l) show (in half-tone dot form) sample patterns of a transparent portion 81a of the shutter 81. These patterns can be stored in a pattern memory portion provided in the shutter control portion 84 and then, when a prescribed pattern is needed, the pattern of the shutter 81 can be switched between such stored patterns by the use of pattern switching signals.

Figure 11:
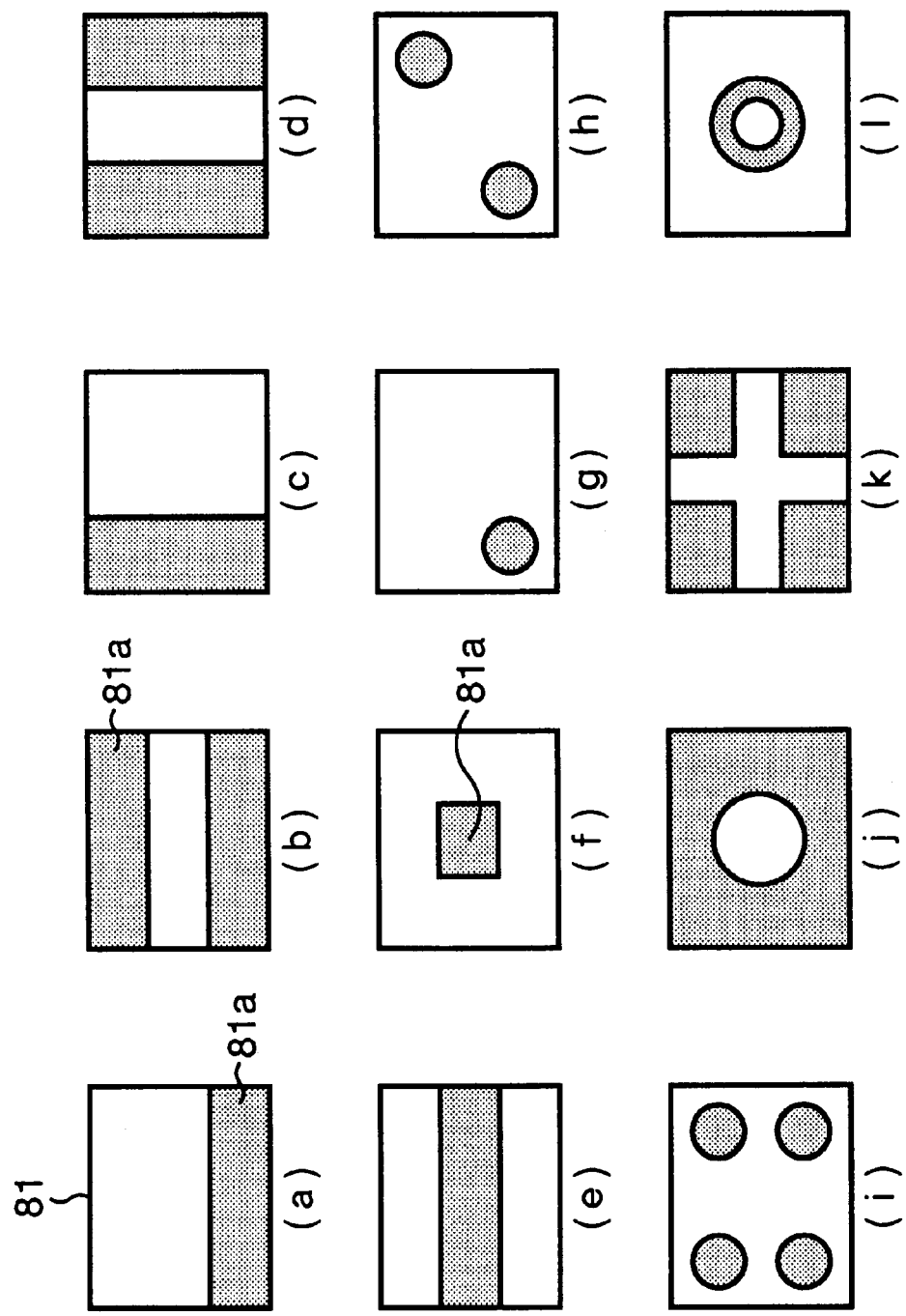
FIG. 11 is a drawing showing sample patterns of transparent portions of the optical shutter.
Figure 12:
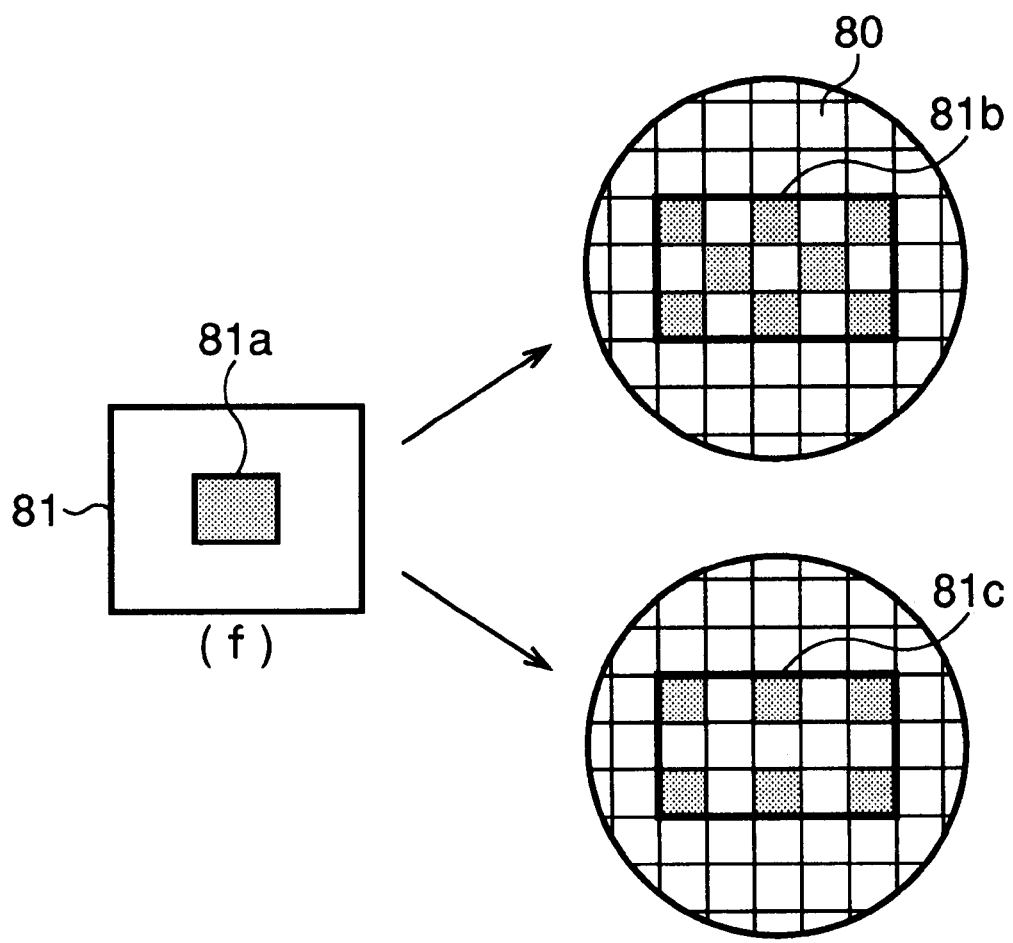
FIG. 12 is a drawing showing another sample pattern of transparent portions of the optical shutter.

At this point, it should be mentioned that it is not necessary for all of the elements within the transparent portions 81a shown in FIG. 11 to be transparent. For example, FIG. 12 shows alternate embodiments of the pattern shown in FIG. 11(f), in which the amount of light that passes through the shutter is controlled by having only a portion (e.g., 50%) of the elements 80 within the transparent portion of the shutter 81 become transparent, as shown by the transparent portions 81b, 81c of FIG. 12. As another option, it is possible to change the degree of transparency of the elements 80 in accordance with their relative position within the transparent portion.

Further, in the case where there is too much brightness when carrying out an observation due to a much larger quantity of light shining along the optical axis than that shining in other directions, in addition to being able to reduce the quantity of such light by adjusting the brightness of the light source, it is also possible to reduce the quantity of such light by adjusting the degree of transparency of the elements of the transparent portions 81b, 81c shown in FIG. 12.

Now, in the embodiment described above, each element of the shutter 81 is basically designed to be in either one of two states, namely a transparent state or an opaque state. However, by constructing the shutter 81 with elements that can be controlled to adjust the amount of light that can pass therethrough, it becomes possible to control the amount of light that passes through each of such elements, and this makes it possible to finely adjust the amount of light that passes through the shutter 81.

Thus, by the use of pattern switching signals, the above-described patterns can instantly be switched to match the optical characteristics of the object being observed. As a result, there is no need to move or exchange a mask plate like that shown in FIG. 9, and this makes it possible to achieve an even greater observation efficiency.

Now, in the case where a plurality of transparent portions are formed in the shutter 81, the position of the light source changes in accordance with the size of such transparent portions. For example, when the transparent portion is as small as a pin hole, the light source is positioned at the position of the shutter 81, and when the transparent portion is large, the light source is positioned at the position of the diffusion plate 73. In this regard, because such changes in the position of the light source can make it difficult to adjust the illumination angle of the light shining on an observation object, it is preferred that the distance "d" (see FIG. 10) between the diffusion plate 73 and the shutter 81 be as small as possible.

Further, even though the optical shutter 81 and lens 11 are fixed in the embodiment shown in FIG. 10, by mounting the optical shutter 81 together with lens 11 or diffusion plate 73 on a moving stage which can move along at least one axis of movement, for example, along the optical axis of the lens 11, it becomes possible to create divergent, convergent and parallel light rays.

Furthermore, it is also possible to utilize a commercially used liquid crystal projector in the construction of the present embodiment. In this case, the optical shutter 81 is positioned in the vicinity of the focal point of the lens 11 in order to illuminate the observation portion 3a with roughly parallel light rays. Further, the optical shutter is not limited to the electrical-type optical shutter described above, and it is also possible to use a mechanical shutter or the like.

Eighth Embodiment

FIG. 13 is a perspective view of a main portion of a bar code labelling apparatus which utilizes a lighting apparatus according to the present invention. In the bar code labelling apparatus shown in FIG. 13, the identification marks on a semiconductor wafer are read out, and then a bar code corresponding to such identification marks is applied to a ring frame or tape described hereinbelow.

As shown in FIG. 13, a semiconductor wafer 75 is mounted on top of a dicing tape 77, with a circumferential portion of the dicing tape 77 being adhered to a ring frame 79 for supporting wafers (hereinbelow, these elements will be referred to as a "work"). Further, identification marks are provided on the semiconductor wafer 75, and notches 79a are formed at two prescribed locations in an outer portion of the ring frame 79.

The "work" is housed within a supply cassette 81, and the ring frames 79 are mounted one at a time onto a stage 83 by a chuck arm or the like of a conveying device (not shown in the drawing). Further, the stage 83 has pins 83a provided at prescribed locations so as to mate with the notches 79a of the ring frame 79. Furthermore, formed in the vertical direction in the stage 83 is a plurality of small holes which communicate with a suction device, and by activating such suction device after the "work" has reached a prescribed position on the stage 83, it is possible to use the suction force generated thereby to fix the "work" to the stage 83. Further, such suction reduces warping and the like for the wafer 75.

The stage 83 is disposed on an X-Y motion device which is equipped with a rotation device to enable the stage 83 to be rotated about its center. This rotation device is not limited to any specific range of rotation, and it is possible, for example, for the rotation device to rotate 90° at a time to the four angular positions 0°, 90°, 180° and 270°.

Now, after the stage 83 has moved the "work" mounted thereon to a position for reading with a CCD camera 5, the identification marks 75a are read out. In this connection, FIG. 13 further shows an illumination box 85 which holds an illumination apparatus according to any one of the above-described first through seventh embodiments of the present invention. Namely, the illumination apparatus inside the illumination box 85 is adjusted to select an appropriate illuminating angle and illuminating angle distribution in order to obtain an illumination that will create a high contrast between the identification marks 75a and the surrounding portions thereof. At this time, if the identification marks 75a are not in the proper position for reading with the camera 5, it is possible to adjust the position of the stage 83 by either rotating it with the rotation device or moving it with the X-Y motion device.

Now, after the illumination light reflects off the wafer 75 and enters the CCD-camera 5, the camera 5 outputs image signals to an image processing device 7 for reading characters, and this enables the identification marks 75a to be read out. Then, the readout results are sent to a bar code printing device 87, where a bar code is printed in accordance with the readout results (i.e., the identification marks 75a) onto a bar code label 89 by a high speed thermal printer or the like provided in the bar code printing device 87, with the bar code label 89 being issued from an issuance port 87a. A bar code affixing vacuum chuck 93 then uses suction to hold the printed surface of the issued bar code label. For this purpose, the bar code affixing vacuum chuck 93 is connected to a vacuum suction hose 93a. Then, the "work" is sent to a bar code label affixing position (i.e., the position of the printing device 87 in this example) where the bar code label 89 is affixed to a prescribed position on the dicing tape 77 or ring frame 79 by operating a drive device 91 to drive the bar code affixing vacuum chuck 93. In this connection, the bar code label affixing position can be adjusted by either rotating the stage 83 with the rotation device or moving it with the X-Y motion device.

After the bar code label has been affixed, a bar code reader 95 is driven and the affixed label is read out, with the results thereof being compared with the results from the image processing device 7 to see if the two results match each other, and if they do not match, the above process is repeated to issue and affix another bar code label.

Once a match is confirmed, the "work" is conveyed to the housing cassette 97 and housed therein. Alternatively, the "work" may be returned to the original supply cassette 81 (as shown by the broken arrow in FIG. 13).

By using the above-described bar code labelling apparatus, it is possible to carry out an automatic process for converting the identification marks on semiconductor wafers into bar codes. Up to now, identification marks on wafers and the like have been read out by direct visual observation or by a reading device, and because reading devices generally lead to higher costs, such costs make it difficult to arrange a reading device for use at each manufacturing step. Thus, with regards to automation of the processing steps for manufacturing semiconductor wafers, it has been extremely difficult up to now to achieve an automatic reading.

In this connection, by using a bar code affixing apparatus like the one described above, it becomes possible to easily read out identification marks of semiconductor wafers by converting such identification marks into bar codes, and this in turn makes it possible to plan for automation of later processes. For example, it becomes possible to carry out CIM (Computer Integrated Manufacturing) for the assembly process, construct a mapping system for managing each wafer IC, construct a system for managing wafer lot information, etc., and this results in a wide improvement in productivity. Further, by providing the lighting apparatus according to the present invention in a bar code labelling apparatus like the one described above, it is possible to provide the most appropriate illumination for semiconductor wafers, and the use of such lighting apparatus makes it possible to accurately read out the identification marks on the wafers. Of course, the above-described bar code labelling apparatus is not limited to use for semiconductor wafers, and it is possible to use such bar code labelling apparatus for converting patterns and marks read out from insulation substrates, such as glass, ceramic and the like, into bar codes.

The lighting apparatus according to the present invention is not limited to use in bar code labelling apparatuses, and it is generally possible to utilize the lighting apparatus of the present invention in a wide variety of apparatuses. For example, it is possible for the lighting apparatus according to the present invention to be used in character reading apparatuses, pattern measuring apparatuses, and other recognition apparatuses and measuring apparatuses, in which the lighting apparatus is used to illuminate an object so that information can be read out based on illumination light which either passes through the object or is reflected therefrom.

In general, the lighting apparatus according to the present invention makes it possible to easily carry out fine adjustments of the illuminating angle and the illuminating angle distribution. In other words, the present invention makes it possible to easily create a plurality of illuminating angles, and create divergent, convergent and parallel illumination light. As a result, in addition to greatly eliminating the troublesome adjustments required for the optical systems of prior art observation apparatuses in order to deal with dispersion of optical characteristics and the like arising during the manufacturing process and the like of the observation object, the lighting apparatus according to the present invention also makes it possible to easily establish the most appropriate illumination conditions for illuminating the observation object. Furthermore, even in the case where it is difficult to carry out an observation under one observation condition due to a large dispersion in the optical characteristics of the observation object, by examining a plurality of illumination conditions in advance, it is possible to easily switch between such illumination conditions with very little effort required by an operator.

Further, in order to change the illuminating angle with prior art lighting apparatuses, many elements have to be adjusted, such as the light-emitting portion, optical system, object, camera and the like. However, with the lighting apparatus of the present invention, the illuminating angle and the like can be changed by only adjusting the light-emitting portion, and such adjustments can be carried out very easily and quickly.

Moreover, by combining the lighting apparatus according to the present invention with an automatic conveying device for conveying observation objects, it is possible to easily create an automatic observation apparatus, and it is also possible to use various recognition devices or measuring devices, such as a character reading device or pattern measuring device, as an image processing device which can receive outputs from a camera.

What is claimed is:

1. A lighting apparatus for illuminating an object so as to achieve an optimum degree of contrast, comprising:

light emitting means for emitting light to be directed toward said object;

optical means disposed between said light emitting means and said object for directing the light toward said object in substantially parallel beams of light; and altering means, operatively associated with at least one of said light emitting means and said optical means, for altering the light as it is directed toward the object so as to produce light having various illuminating angles and various illuminating angle distributions, whereby to illuminate the object at at least one illumination angle which achieves the optimum degree of contrast;

wherein said altering means includes moving means for moving said light emitting means in a direction parallel to a focal plane of said optical means in order to change the illuminating angle.

2. The apparatus of claim 1, wherein said moving means moves said light emitting means along at least one axis.

3. The apparatus of claim 2, wherein said light emitting means comprises a plurality of light emitting portions.

4. The apparatus of claim 3, further comprising selecting means for selecting at least one of said light emitting portions for activation to emit light.

5. The apparatus of claim 1, wherein said light emitting means comprises light emitting end portions of light guiding elements.

6. The apparatus of claim 1, wherein said light emitting means is arranged in the vicinity of a front focal plane of said optical means.

7. The apparatus of claim 1, wherein said altering means comprises a mask plate including at least one aperture portion, said mask plate being arranged between said light emitting means and said optical means, said altering means further comprising moving means for moving said mask plate relative to said optical means in order to change the illuminating angle.

8. The apparatus of claim 1, wherein said altering means comprises an optical shutter arranged between said light emitting means and said optical means, and drive means for driving said optical shutter in order to alter the light emitted by said light emitting means prior to reaching said optical means.

9. The apparatus of claim 1, wherein said light emitting means is arranged in the vicinity of a front focal plane of said optical means.

* * * * *